(12) United States Patent
Van Gompel et al.

(10) Patent No.: US 7,404,813 B2
(45) Date of Patent: Jul. 29, 2008

(54) UNDERGARMENT HAVING CROTCH MEMBER WITH UNATTACHED END PORTION

(75) Inventors: Paul T. Van Gompel, Hortonville, WI (US); David F. Bishop, Appleton, WI (US); Monica S. Diaz, Woodstock, GA (US); Jacqueline A. Gross, Neenah, WI (US); Cindy L. Price, Appleton, WI (US); Monica G. Varriale, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 467 days.

(21) Appl. No.: 10/316,779

(22) Filed: Dec. 11, 2002

(65) Prior Publication Data

US 2004/0116886 A1    Jun. 17, 2004

(51) Int. Cl.
*A61F 13/15* (2006.01)

(52) U.S. Cl. ............ 604/394; 604/385.03; 604/385.22; 604/392; 604/393

(58) Field of Classification Search ............ 604/385.01, 604/385.03, 385.14, 385.22, 385.24–385.29, 604/392–399
See application file for complete search history.

(56) References Cited

U.S. PATENT DOCUMENTS

| | | | |
|---|---|---|---|
| 4,022,212 A | 5/1977 | Lovison | |
| 4,756,709 A | 7/1988 | Stevens | |
| 4,808,176 A | 2/1989 | Kielpikowski | |
| 4,834,738 A | 5/1989 | Kielpikowski | |
| 5,116,662 A | 5/1992 | Morman | |
| 5,330,598 A | 7/1994 | Erdman et al. | |
| 5,445,628 A * | 8/1995 | Gipson et al. | ............... 604/392 |
| 5,464,401 A | 11/1995 | Hasse et al. | |
| 5,527,303 A | 6/1996 | Milby, Jr. et al. | |
| 5,569,232 A | 10/1996 | Roe et al. | |
| 5,704,930 A | 1/1998 | Lavash et al. | |
| 5,772,649 A * | 6/1998 | Siudzinski | ................. 604/386 |
| 5,824,004 A | 10/1998 | Osborn, III et al. | |
| 5,836,932 A | 11/1998 | Buell et al. | |

(Continued)

FOREIGN PATENT DOCUMENTS

EP    0 904 753 A2    3/1999

(Continued)

OTHER PUBLICATIONS

International Search Report for PCT/US03/18168, mailed May 18, 2004, pp. 1-3.

(Continued)

*Primary Examiner*—Michael G. Bogart
(74) *Attorney, Agent, or Firm*—Brinks Hofer Gilson & Lione

(57) ABSTRACT

An undergarment includes a body panel and an crotch member. The crotch member includes first and second terminal edges and laterally opposed side edges. The crotch member has a longitudinally extending length defined between the first and second terminal edges. The crotch member is connected to the body panel at an attachment location, which is longitudinally spaced along the length of the crotch member from the first terminal edge thereof. The crotch member includes an unattached end portion that extends between the attachment location and the first terminal edge and that is unattached to the body panel. Methods of using and manufacturing the undergarment are also provided.

15 Claims, 2 Drawing Sheets

U.S. PATENT DOCUMENTS

| | | | |
|---|---|---|---|
| 5,846,232 A | 12/1998 | Serbiak et al. | |
| 5,993,431 A | 11/1999 | McFall et al. | |
| 5,993,432 A | 11/1999 | Lodge et al. | |
| 5,997,521 A | 12/1999 | Robles et al. | |
| 6,004,306 A | 12/1999 | Robles et al. | |
| 6,099,516 A | 8/2000 | Pozniak et al. | |
| 6,129,720 A | 10/2000 | Blenke et al. | |
| 6,183,458 B1 | 2/2001 | Ahlstrand et al. | |
| 6,186,992 B1 | 2/2001 | Roe et al. | |
| 6,193,701 B1 | 2/2001 | Van Gompel et al. | |
| 6,217,563 B1 | 4/2001 | Van Gompel et al. | |
| 6,240,569 B1 * | 6/2001 | Van Gompel et al. | 2/400 |
| 6,262,331 B1 | 7/2001 | Nakahata et al. | |
| 6,264,641 B1 | 7/2001 | Van Gompel et al. | |
| 6,296,628 B1 | 10/2001 | Mizutani | |
| 6,312,420 B1 * | 11/2001 | Sasaki et al. | 604/385.28 |
| 6,325,787 B1 | 12/2001 | Roe et al. | |
| 6,361,527 B1 | 3/2002 | Van Gompel et al. | |
| 6,371,950 B1 | 4/2002 | Roslansky et al. | |
| 6,648,868 B2 * | 11/2003 | Sayama et al. | 604/385.22 |
| 6,755,808 B2 * | 6/2004 | Balogh et al. | 604/385.28 |
| 2001/0016719 A1 | 8/2001 | Mishima | |
| 2001/0039408 A1 | 11/2001 | Tanji et al. | |
| 2001/0041877 A1 * | 11/2001 | Canuel | 604/385.01 |
| 2001/0047159 A1 | 11/2001 | Mizutani | |
| 2002/0010454 A1 | 1/2002 | Van Gompel et al. | |
| 2002/0028624 A1 | 3/2002 | Mizutani et al. | |
| 2002/0045877 A1 | 4/2002 | Shimada et al. | |
| 2002/0052588 A1 | 5/2002 | Otsubu | |
| 2002/0052589 A1 | 5/2002 | Strand | |
| 2002/0169432 A1 * | 11/2002 | Fell et al. | 604/385.14 |

FOREIGN PATENT DOCUMENTS

| | | |
|---|---|---|
| EP | 0794751 B1 | 6/1999 |
| EP | 0 998 892 A2 | 5/2000 |
| EP | 1 101 469 A | 5/2001 |
| EP | 0 904 753 B1 | 1/2003 |
| GB | 2 253 131 A | 9/1992 |
| GB | 2 268 389 A | 1/1994 |
| JP | 2031755 | 2/1990 |
| JP | 8084747 | 4/1996 |
| JP | 11128267 | 5/1999 |
| JP | 11302955 | 11/1999 |
| JP | 2001140158 | 5/2001 |
| JP | 2001 170107 | 6/2001 |
| WO | WO 99/56688 A1 * | 11/1999 |
| WO | WO 01/15645 | 3/2001 |
| WO | WO 01/82850 A1 | 11/2001 |
| WO | WO 01/82852 A1 | 11/2001 |
| WO | WO 02/091974 A | 11/2002 |

OTHER PUBLICATIONS

International Search Report in corresponding International Application No. PCT/US03/18168, dated Feb. 12, 2004, 8 pages.

* cited by examiner

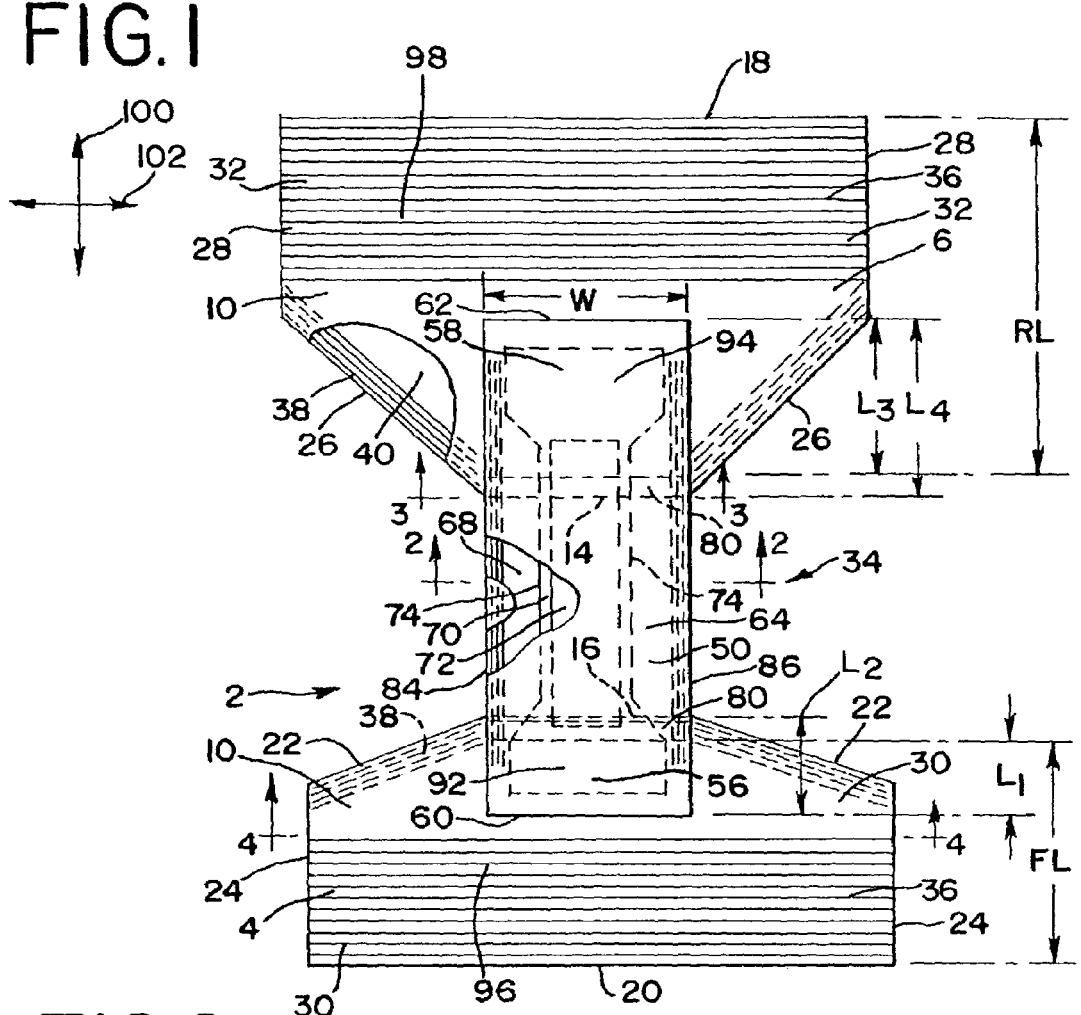
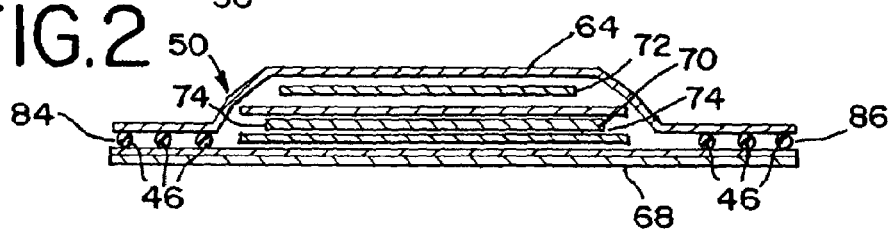
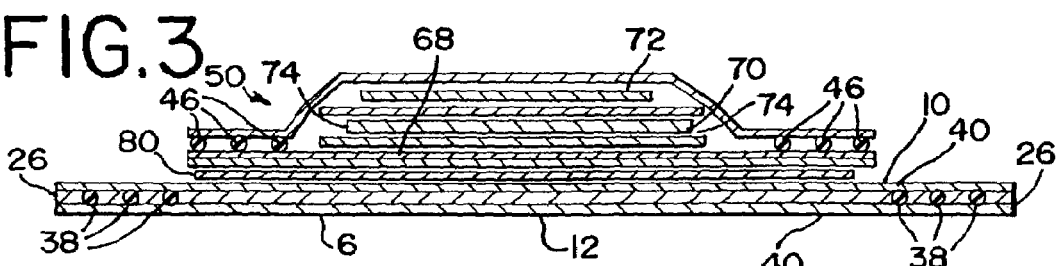
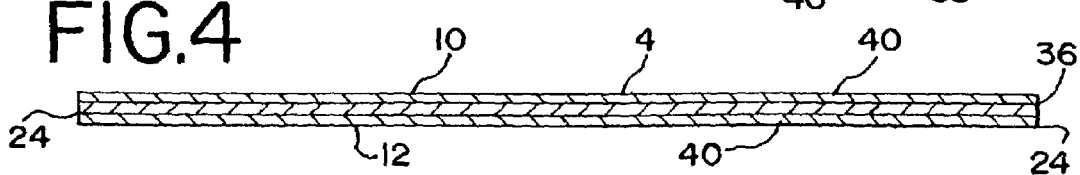

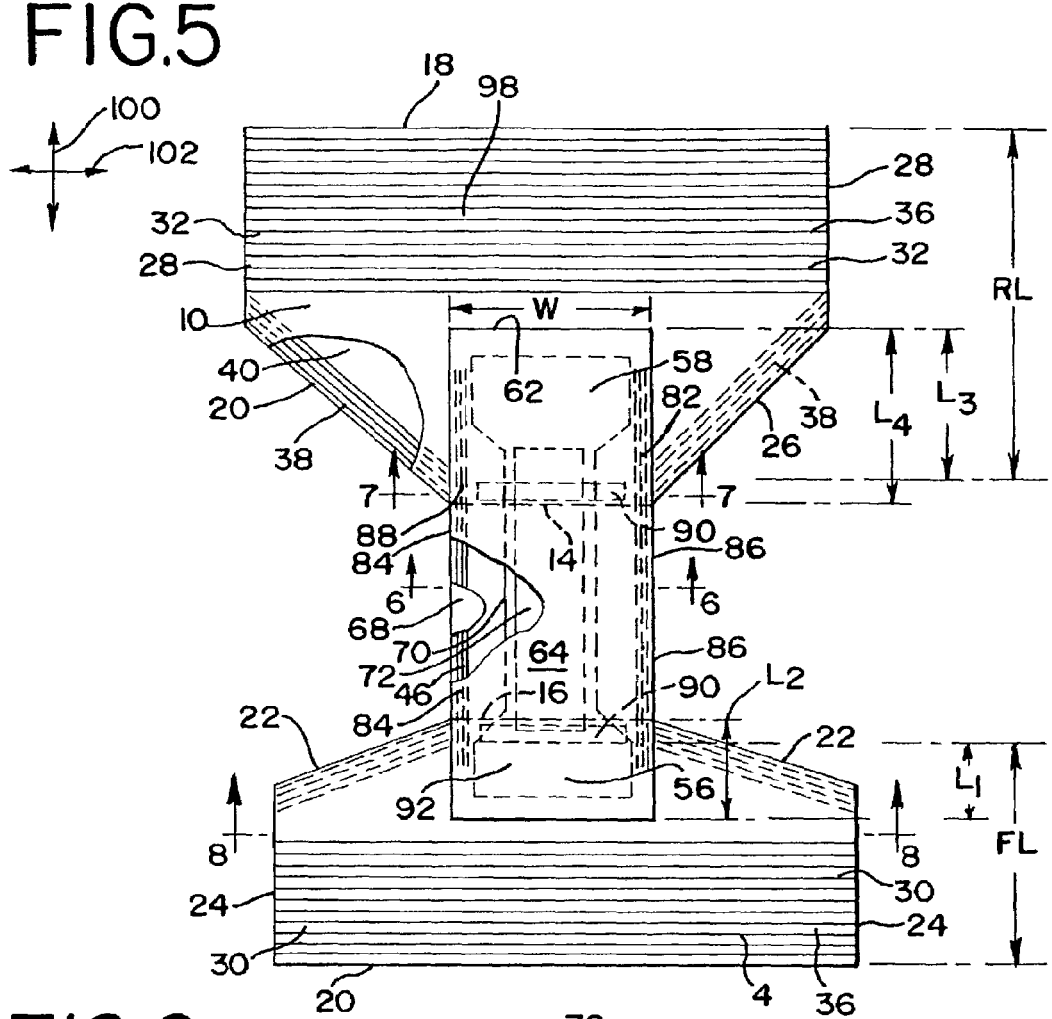
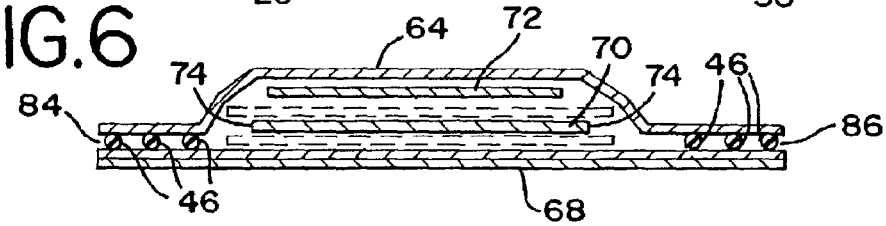
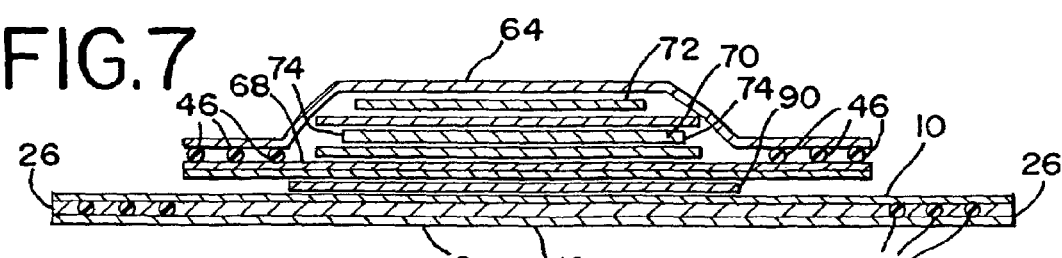
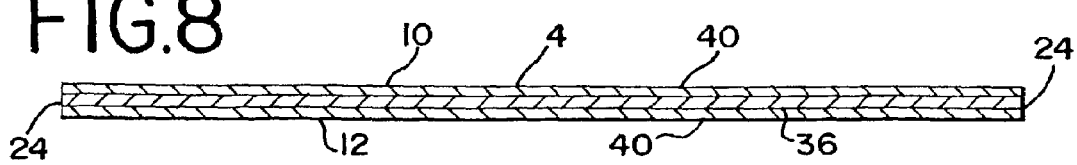

UNDERGARMENT HAVING CROTCH MEMBER WITH UNATTACHED END PORTION

BACKGROUND

The present invention relates generally to an undergarment, and in particular, to an absorbent undergarment that conforms to the body of the user.

Undergarments, for example disposable absorbent garments, often include an absorbent composite and one or more body panels connected to the absorbent composite. Often, the absorbent composites are secured to the body panels along the entire length of the portion of the absorbent composite that overlaps the body panels, and often across the entire width of the absorbent composite as well. As such, the absorbent composite can reduce or otherwise impede the extensibility or elongation of the body panel in both the longitudinal and lateral directions, thereby reducing its ability to conform to the body of the user. In addition, the absorbent composite typically is not able to conform to the body of the user independently of the body panels, and can therefore distort the panels when fitted to a user.

SUMMARY

Briefly stated, in one preferred embodiment, an undergarment includes a body panel and a crotch member. The crotch member includes first and second terminal edges and laterally opposed side edges. The crotch member has a longitudinally extending length defined between the first and second terminal edges. The crotch member is connected to the body panel at an attachment location, which is longitudinally spaced along the length of the crotch member from the first terminal edge thereof. The crotch member includes an unattached end portion that extends between the attachment location and the first terminal edge, and which is unattached to the body panel. In one preferred embodiment, the crotch member is formed as an absorbent composite.

In one preferred embodiment, the body panel includes first and second longitudinally spaced terminal edges. Preferably, the attachment location is located adjacent the second terminal edge of said body panel. In one preferred embodiment, the crotch member has an overlapping portion extending between the second terminal edge of the body panel and the first terminal edge of the crotch member. Preferably, the unattached end portion of the crotch member has a first length and the overlapping portion of the crotch member has a second length, wherein the first length is at least 20 percent of the second length.

In one preferred embodiment, the undergarment includes a first body panel and a second body panel each having first and second longitudinally spaced terminal edges. The crotch member is connected to the second body panel at a second attachment location, which is longitudinally spaced along the length of the crotch member from the second terminal edge thereof and is located adjacent the second terminal edge of the second body panel. Preferably, a second unattached end portion of the crotch member extends between the second attachment location and the second terminal edge of the crotch member and is unattached to the second body panel.

In one preferred embodiment, the crotch member has a width. The attachment location preferably extends across an entirety of the width of the crotch member. In another preferred embodiment, the attachment location extends across only a portion of the width of the crotch member.

In various preferred embodiments, the body panel is longitudinally and/or laterally elongatable. In one preferred embodiment, the body panel has a terminal edge longitudinally spaced from the attachment location, with an unattached region of the body panel being defined therebetween. Preferably, the unattached region of the body panel is elongatable between at least a first and second length without a corresponding elongation of the unattached end portion of the crotch member.

In another aspect, a method of using an undergarment is provided. In one preferred embodiment, the method includes applying an undergarment to the body of a user and elongating at least the unattached region of a body panel in a longitudinal direction without elongating the unattached end portion of the crotch member.

In yet another aspect, a method of assembling an undergarment is provided. In one preferred embodiment, the method includes providing a body panel and a crotch member and overlapping at least a portion of the crotch member with the body panel. The method further includes connecting the crotch member to the body panel at an attachment location, wherein the crotch member comprises an unattached end portion that is unattached to the body panel.

The presently preferred embodiments provide significant advantages over other undergarments, including absorbent garments, and methods for the use and manufacture thereof. For example, the unattached end portions of the crotch member do not restrict or interfere with the elongation and/or conformance of the body panel. In this way, the body panels are allowed to extend or elongate in the longitudinal direction, and also to elongate or stretch in the lateral direction, without restraint from the crotch member, which typically does not exhibit the same elongation properties of the body panels. At the same time, the garment is provided with a relatively fixed crotch length by virtue of the crotch member extending between attachment locations on the first and second body panels.

In addition, in one preferred embodiment, wherein the crotch member is formed as an absorbent composite, the absorbent capacity of the garment can be easily changed simply by increasing the length of the unattached end portion of the absorbent composite, without affecting the conformance, size or fit of the garment.

The foregoing paragraphs have been provided by way of general introduction, and are not intended to limit the scope of the following claims. The presently preferred embodiments, together with further objects and advantages, will be best understood by reference to the following detailed description taken in conjunction with the accompanying drawings.

BRIEF DESCRIPTION OF THE DRAWINGS

Many of the features and dimensions portrayed in the drawings, and in particular the presentation of layer thicknesses and the like, have been somewhat exaggerated for the sake of illustration and clarity.

FIG. 1 is a plan view of a first embodiment of an undergarment taken from the bodyside thereof.

FIG. 2 is a schematic illustration of a cross-sectional view of the undergarment taken along line 2-2 in FIG. 1.

FIG. 3 is a schematic illustration of a cross-sectional view of the undergarment taken along line 3-3 in FIG. 1.

FIG. 4 is a schematic illustration of a cross-sectional view of the undergarment taken along line 4-4 in FIG. 1.

FIG. 5 is a plan view of a second embodiment of an undergarment taken from the bodyside thereof.

FIG. 6 is a schematic illustration of a cross-sectional view of the undergarment taken along line 6-6 in FIG. 5.

FIG. 7 is a schematic illustration of a cross-sectional view of the undergarment taken along line 7-7 in FIG. 5.

FIG. 8 is a schematic illustration of a cross-sectional view of the undergarment taken along line 8-8 in FIG. 5.

DETAILED DESCRIPTION OF THE PRESENTLY PREFERRED EMBODIMENTS

It should be understood that the term "longitudinal," as used herein, means of or relating to length or the lengthwise direction, and in particular, the direction running between the front and back of the user. The term "laterally," as used herein means situated on, directed toward or running from side to side, and in particular, a direction running from the left to the right of a user. The terms "upper," "lower," "inner", and, "outer" as used herein are intended to indicate the direction relative to the user wearing an absorbent garment over the crotch region, while the terms "inboard" and "outboard" refer to the directions relative to a centerline of the garment. For example, the terms "inner" and "upper" refer to a "bodyside," which means the side closest to the body of the user, while the terms "outer" and "lower" refer to a "garment side". The term "bodyside" should not be interpreted to mean in contact with the body of the user, but rather simply means the side that would face toward the body of the user, regardless of whether the absorbent garment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the absorbent garment is actually being worn by a user, regardless of whether any such outer garments are actually worn and regardless of whether there may be intervening layers between the component and any outer garment.

It should be understood that the term "undergarment" refers to a garment worn next to the body, regardless of whether additional garments are worn on top thereof. Accordingly, and for example without limitation, a diaper is an undergarment, even if worn only by itself.

Referring to FIGS. 1 and 5, an undergarment 2 includes a first, front body panel 4 and a second, rear body panel 6. The first and second body panels each have an inner, bodyside surface 10 an outer, garment side surface 12 and a length, which is less the overall length of the under garment. Each of the first and second body panels has a first and second longitudinally opposed terminal end edges 16, 14, 20, 18, and outer side edges, including a tapered edge 22, 26 and an outboard edge 24, 28 formed along the outer periphery of laterally opposed ear portions 30, 32. Alternatively, one or both of the front and rear body panels is configured without a tapered side edge, and instead is formed with a terminal end edge extending along the entire width of the body panel between the opposite outboard edges. Of course, it should be understood that the terminal edges can assume many shapes, including various scallop or sinusoidal shapes.

Referring to FIGS. 1 and 5, the first terminal edges 16, 14 of the first and second body panels are longitudinally spaced to form an opening 34 or gap therebetween in the crotch region of the garment, while the second terminal edges 20, 18 of the first and second body panels are located proximate to and define front and back waist edges respectively. A plurality of, meaning two or more, laterally extending elastic elements 36 can be secured to each of the first and second body panels. Likewise, one or more leg elastic elements 38 can be secured along the tapered side edge of the body panels to form a gasket with the leg of the user. The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

For example, as shown in FIGS. 1, 3, 5 and 7, each panel can be made of an elasticized composite panel material comprising two non-woven substrates 40 with the plurality of elastic strands 38, 36 sandwiched therebetween. The elastic strands are positioned in the waist regions and along the leg perimeters. A portion of the leg elastic elements 38 can extend under a side portion of an absorbent composite 50.

Preferably, the outboard edges 24, 28 of the front and rear body panels are connected, for example by bonding or sewing, to create a seam of a pant garment. When secured in this way, the body panels and absorbent composite define a pair of leg openings 120 on each side of the absorbent composite 50. Alternatively, one or more fastening members can be attached to one or both of the front and rear body panels and releasably or fixedly engage the other of the front and rear body panels. Various landing materials can be incorporated into the body panels as desired to engage the fastening members. The fastening members can be made of a hook and loop combination, such as a VELCRO® fastening system, or can have adhesive or other bonding agents, such a pressure sensitive adhesives, applied to one surface thereof. Various hook configurations are described in U.S. Pat. No. 5,845,375 to Miller et al., U.S. Pat. No. 6,132,660 to Kampfer, U.S. Pat. No. 6,000,106 to Kampfer, U.S. Pat. No. 5,868,987 to Kampfer, U.S. Pat. No. 4,894,060 to Nestegard, and U.S. Pat. No. 6,190,594 B1 to Gorman, the entire disclosures of which are incorporated by reference herein. Some examples of suitable hook fasteners are the various CS600 hook fasteners manufactured by Minnesota Mining and Manufacturing Co., St. Paul Minn.

In yet another alternative embodiment, the front and rear body panels can be formed integrally, for example as a single panel extending around the waist and hips of the user. In yet another alternative embodiment, the outboard edges can be connected to create a seam in combination with fastening tabs, which can be used for example and without limitation to secure the body panels across a line of weakness, such as a perforation. The line of weakness can be formed for example along a breakable seam between the front and rear body panels, or along a length of one or both of the front and rear body panels.

In particular aspects of the invention, either or both of the body panels may be composed of a wide range of materials with various basis weights and properties. For example, the body panel material may include knitted or woven fabrics, nonwoven fabrics, polymer films, laminates, and the like, as well as combinations thereof. In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along the lateral article width. Examples of such elastomeric materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,414,470, 4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites.

Preferably, the body panels are breathable, cloth-like, multi-directional nonwoven laminates with stretch and/or extensible properties. In one preferred embodiment, the non-woven layers are pre-necked, preferably between about 10% and about 80%, in the longitudinal direction 100, which provides extensibility in the longitudinal direction with minimum force.

The terms "extensible," "extensibility," and variations thereof as used herein means capable of being extended, and providing a selected elongation when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occur at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the preferred non-woven material provides an increase in surface area without the retractive force of elastomeric materials. The term "non-woven" web or material, as used herein, means a web having a structure of individual fibers or filaments that are interlaid, but not in an identifiable manner and without the aid of textile weaving or knitting, as in a knitted or woven fabric. In one preferred embodiment, body panel is extensible in at least the cross-direction, or longitudinal direction, with the material providing an elongation of at least about 1 cm when subjected to a tensile stress of 11.8 grams per cm. In addition, the body panel preferably provides a substantially permanent deformation of at least about 20% when it is subjected to a tensile stress of 19.70 grams per cm and is then allowed to relax under a zero applied stress for a period of 1 minute. Of course, it should be understood that the body panel can also be made extensible in the lateral direction.

In one preferred embodiment, the front and rear body panels 4, 6 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to to the desired direction of neck-down. Processes that may be used to constrict a material in such a manner include, for example and without limitation, drawing processes. The elastics are then elongated in the machine direction and secured to the body panel material. The elastics are then allowed to retract so as to gather the necked spunbond material in the lateral (machine) direction 102 thereby creating an elastically gathered non-woven body panel with longitudinal extensibility. The term "gather," and variations thereof, as used herein means puckered, or contracted into folds or wrinkles, which should be understood as including micro-pleats. In this way, the body panel can be elongated in both the longitudinal and lateral direction to conform to the body of the user when the garment is applied thereto. In particular, as the user pulls the garment up over their hips, the non-woven laminate body panels stretch in the lateral direction 102 while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements 36, incorporated in one preferred embodiment, will increase.

Referring FIGS. 1-3 and 5-7, the crotch member 50 has first and second longitudinally opposed terminal end edges 60, 62. In one preferred embodiment, wherein the undergarment is formed as a disposable absorbent garment, the crotch member is formed as an absorbent composite, which includes a substantially liquid permeable topsheet 64, or liner, and a substantially liquid impermeable backsheet 68, or barrier layer. A retention portion 70 is disposed or sandwiched between the topsheet and the backsheet, which are connected, at least along their peripheral edges. The absorbent composite, and in particular the retention portion, can be made in many different shapes, including rectangular and hour-glass shapes. It should be understood that the term "absorbent composite" as used herein refers to any material or assembly capable of absorbing liquids or bodily exudates, and may be comprised of a single material or component, for example a retention portion. It should also be understood that the term "crotch member" refers to any member made of any material, including for example and without limitation those described herein with respect to the body panels and absorbent composites, and is not limited to absorbent composites and/or materials. For example, the crotch member may be made of one or more layers of a non-woven material.

In one preferred embodiment, the topsheet and backsheet of the absorbent composite can be minimally attached, e.g. at the peripheral edges, or they can be attached across substantially the entire surface area thereof. The topsheet and backsheet can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. Additional layers, including for example, a surge layer 72, can also be incorporated into the absorbent composite. Preferably, the surge layer does not run the entire length of the absorbent composite and is shorter than the retention portion. In alternative configurations, the topsheet is indirectly joined to the backsheet by affixing the topsheet to intermediate layers, such as the surge layer or retention portion, which in turn is affixed to the backsheet. Preferably, longitudinally extending elastic elements 46 are secured along the sides of the absorbent composite, for example between the top sheet and backsheet.

The topsheet 64 presents a body-facing surface that is compliant, soft-feeling, and non-irritating to the wearer's skin. Further, the topsheet 64 can be less hydrophilic than retention portion 70, and is sufficiently porous to be liquid permeable, permitting liquid to readily penetrate through its thickness to reach the retention portion. A suitable topsheet layer 64 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The topsheet layer 64 is typically employed to help isolate the wearer's skin from liquids held in the retention portion.

Various woven and nonwoven fabrics can be used for topsheet 64. For example, the topsheet may be composed of a meltblown or spunbonded web of the desired fibers, and may also be a bonded-carded-web. The various fabrics can be composed of natural fibers, synthetic fibers or combinations thereof.

The topsheet fabrics may be composed of a substantially hydrophobic material, and the hydrophobic material may optionally be treated with a surfactant or otherwise process to impart a desired level of wettability and hydrophilicity. In a particular embodiment of the invention, the topsheet 64 is a nonwoven, spunbond polypropylene fabric composed of about 2.8-3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various embodiments, as described below, the topsheet can be made of extensible materials, as described with respect to the body panels and backsheet. For example, the topsheet can be prenecked for extensibility.

The backsheet 68 is preferably liquid impermeable, but may be liquid permeable, e.g., when a barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In other alternative constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers) . A material of this type has been employed to form the outercover of a HUGGIES® Ultratrim Disposable Diaper, which has been commercially available from Kimberly-Clark Corporation.

In one alternative embodiment, the garment may include a separate outercover component that is extends over the absorbent composite and the body panels. The outercover can be joined to one or more of the absorbent composite and/or body panels. The outercover can be made of any of the materials described herein.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof. In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet also can be expandable, for example when it has one or more folds, e.g., one or more z-folds (not shown), or can be both extensible and expandable. The term "expandable" as used herein means to enlarge or to increase the extent or area, lateral and/or longitudinal, thereof, e.g., by unfolding one or more folds. Likewise, the term "elongated," "elongatable," and variations thereof, broadly means to enlarge or increase the extent or length or width thereof, for example by unfolding, stretching or deforming or other similar actions.

The retention portion 70 has laterally opposed side edges 74 and preferably can be made of a single or dual layer of absorbent material, which can be any material that tends to swell or expand as it absorbs exudates, including various liquids and/or fluids excreted or exuded by the user. The retention portion preferably has an hour-glass shape with enlarged end regions. Alternatively, the retention portion can include a folded or multi-layered configuration. The retention portion preferably has a length substantially equal to, or slightly shorter than, the length of the absorbent composite. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

In one preferred embodiment, the retention portion 70 is preferably made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and U.S. Pat. No. 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

Referring to FIGS. 1, 3, 5 and 7, the opposite garment side of the end regions 56, 58 of the absorbent composite, and in particular, the outer, garment side surface of the backsheet 68, are secured to the bodyside surface of the longitudinally opposed crotch ends of the first and second body panels 4, 6. Preferably, the garment side surface of the end regions 56, 58 overlap and are connected to the bodyside surface of the body panels along a lateral attachment location 80. In an alternative embodiment, the absorbent composite, for example the bodyside surface of the top sheet, is secured to the garment side surface of the first and second body panels. It should be understood that the absorbent composite can be secured using any of the methods of attachment described above, including for example and without limitation, adhesive bonds, sonic bonds, thermal bonds, pinning, stitching or other attachment techniques known in the art, as well as combinations thereof.

Referring to FIG. 1, in one embodiment, the attachment location 80 extends across the entirety of the width (W) of the absorbent composite at that location. It should be understood that the term "location" means any region, dot, position or side, and is not limited to the laterally extending lines shown in the Figures. For example, the location could comprise a series of laterally extending dots or points. Conversely, the location could comprise a continuous region or area attachment extending across the lateral width (W) of the absorbent composite between the outboard edges of the attached region of the absorbent composite.

In an alternative preferred embodiment, shown in FIG. 5, the attachment location 90 extends laterally across only a portion of the width of the absorbent composite. In various embodiments, the attachment location has a width of between about 10% to 90% of the width (W) of the absorbent composite, alternatively about 20% to 80% of the width (W) of the absorbent composite, and about 30% to 70% of the width (W) of the absorbent composite. In this embodiment, side margins 88, 82 are preferably formed along the entire longitudinal extent of the portion of the absorbent composite that overlaps the body panels, and also extend along the crotch and the absorbent composite between the body panels. The side margins 88, 82 are not attached to the body panels 4, 6 and terminate in free edges 84, 86.

In either embodiment, the absorbent composite includes a first and second opposite unattached end portions 92, 94 that overlie the body panels and extend respectively between the attachment locations 80, 90 and the terminal ends 60, 62 of the absorbent composite and have a length (L1, L3). The unattached end portions 92, 94 are not attached to the body panels 4, 6. Likewise, the body panels 4, 6 have an unattached region 96, 98 extending between the attachment locations 80, 90 and the terminal ends 16, 20. Again the unattached regions 96, 98 of the body panels 4, 6 are not attached to the absorbent composite 50. In a relaxed, pre-extension state, the unattached regions 96, 98 have a length (FL and RL).

When put in use, the body panels 4, 6, and in particular the unattached regions 96, 98, can be elongated, for example by extension, from the length FL and RL to a length FL' and RL', which is greater than FL and RL respectively. At the same time, the unattached end portions 92, 94 of the absorbent composite are not elongated, since they are unattached to the body panels 4, 6. In this way, the absorbent composite 50 does not adversely affect the extensibility of the body panels 4, 6 in the longitudinal direction 100. At the same time, the body panels 4, 6 can be elongated, for example by stretching, in the lateral direction 102, again without any adverse effect from the absorbent composite 50, since it is preferably attached along only the terminal edges 14, 16 of the body panels.

The overlapping portions 56, 58, or end regions, of the absorbent composite 50 have a length (L2, L4) measured between the terminal edge 14, 16 of the body panels 4, 6 and the terminal edge 60, 62 of the absorbent composite 50 respectively. Preferably, the lengths L1, L3 of the unattached end portions 92, 94, and also the total surface areas of the unattached end portions, are at least 20% of the lengths L2, L4, and also the total surface areas of the overlapping portions 56, 58, respectively. Of course, it should be understood that the different lengths of the unattached end portions, overlapping portions and unattached regions can be the same or different relative to the front and rear body panels.

The length of the absorbent composite 50 can be varied to provide more or less absorbent capacity without affecting the overall size or fit of the garment. At the same time, when the body panels are elongated, by extensible deformation or stretching, the length of the crotch region or gap 34, measured between the terminal edges 14, 16 of the body panels, remains relatively fixed, due to the preferably non-extensible configuration of the absorbent composite.

In the embodiments shown in FIGS. 1 and 5, one or more elastic elements 46, shown as three, are secured in the side margins of the absorbent composite between the topsheet and backsheet, and extend longitudinally along a portion of the side margins on each side of the absorbent composite. Preferably, the elastic elements 46 extend along the side margins of the absorbent composite between the body panels and overlap a portion of each body panel 4, 6. The length of the elastic elements is preferably between about 5% and 100% of the length of the absorbent composite. The function of the elastic elements in the side margins of the absorbent composite are to shorten the length of the side margin which pulls the side margins inwardly to form a three-dimensional profile so as to seal or gasket against the body of the user. The elastic elements can be positioned at various laterally spaced positions, depending on the amount of shortening and upward lift desired. The elastic elements can be made of ribbon, films, sprays of elastic, or other elastic configurations know in the art.

In yet another embodiment, a body panel is continuous from the rear of the garment through the crotch region to the front of the garment. In such an embodiment, the absorbent composite can be attached to the front, rear and crotch portions of the body panel. In essence, a crotch body panel extends between and connects a front and rear body panel, with the three pieces being made separately or integrally formed as a single unit. The body panel is preferably made of continuous sheets or layers that form the three regions, although it should be understood that separate pieces can be joined, e.g., by bonding, stitching etc., to form the full length body panel. In this alternative embodiment, the absorbent composite is secured to the body panel along one or two attachment locations spaced from the terminal ends of the body panel so as to form the unattached end portions of the absorbent composite. In one embodiment, the absorbent composite is secured to the body panel along a single lateral attachment location, with the unattached end portions extending longitudinally from opposite edges of the attachment location. For example, the attachment location can be positioned in the middle of the crotch portion.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. An undergarment comprising:
a first body panel comprising first and second longitudinally spaced terminal edges;
a second body panel comprising first and second longitudinally spaced terminal edges; and
a crotch member comprising first and second terminal edges and laterally opposed side edges, said crotch member having a longitudinally extending length defined between said first and second terminal edges of said crotch member, wherein said crotch member is non-releasably connected to said first body panel at a first attachment location located at said first terminal edge of said first body panel, wherein said first attachment location is longitudinally spaced along said length of said crotch member from said first terminal edge thereof, and wherein said crotch member comprises a first unattached end portion extending between said first attachment location and said first terminal edge of said crotch member, wherein said first unattached end portion is unattached to said first body panel, wherein said crotch member comprises an overlapping portion extending between said first terminal edge of said first body panel and said first terminal edge of said crotch member, wherein said first unattached end portion of said crotch member has a first length and said overlapping portion of said crotch member has a second length, wherein said first length is at least 20 percent of said second length, and wherein said crotch member is connected to said second body panel at a second attachment location, wherein said second attachment location is longitudinally spaced along said length of said crotch member from said second terminal edge thereof and is located at said first terminal edge of said second body panel, and wherein a second unattached end portion of said crotch member extends between said second attachment location and said second terminal edge of said crotch member, wherein said second unattached end portion is unattached to said second body panel.

2. The undergarment of claim 1 wherein said first length is at least 50 percent of said second length.

3. The undergarment of claim 1 wherein said crotch member has a width, and wherein said first attachment location extends across an entirety of said width of said crotch member.

4. The undergarment of claim 1 wherein said crotch member has a width, and wherein said first attachment location extends across only a portion of said width of said crotch member.

5. The undergarment of claim 1 wherein said first body panel is longitudinally extensible.

6. The undergarment of claim 5 wherein said second terminal edge of said first body panel is longitudinally spaced from said first attachment location and defines an unattached region of said first body panel therebetween, and wherein said unattached region of said first body panel is elongatable between at least a first and second length without a corresponding elongation of said first unattached end portion of said crotch member.

7. The undergarment of claim 5 wherein said first body panel has a longitudinal elongation of at least about 1 cm when subjected to a tensile stress of 11.8 grams/cm.

8. The undergarment of claim 7 wherein said first body panel has a substantially permanent deformation of at least about 20% when subjected to a tensile stress of 19.70 grams/cm and then allowed to relax under a zero applied stress for a period of about 1 minute.

9. The undergarment of claim 1 wherein said first body panel is laterally elongatable.

10. The undergarment of claim 9 wherein said first body panel comprise laterally extending elastic elements.

11. The undergarment of claim 1 wherein said first body panel has a bodyside and said crotch member has a garment side, wherein said garment side of said crotch member is secured to said bodyside of said first body panel.

12. The undergarment of claim 1 wherein said crotch member comprises an absorbent component.

13. An undergarment comprising:
a first body panel having first and second longitudinally spaced terminal edges and laterally spaced opposite sides, wherein at least a portion of said first body panel is longitudinally extensible between said first and second longitudinally spaced terminal edges, said first body panel having a longitudinal elongation of at least about 1 cm when subjected to a tensile stress of 11.8 grams/cm and a substantially permanent deformation of at least about 20% when subjected to a tensile stress of 19.70 grams/cm and then allowed to relax under a zero applied stress for a period of about 1 minute, and wherein said first body panel is laterally elongatable;
a second body panel having first and second longitudinally spaced terminal edges; and
a crotch member comprising first and second longitudinally spaced terminal edges and laterally spaced opposite side edges, wherein said crotch member is connected to said first body panel at a first attachment location located at said first terminal edge of said first body panel, wherein said first attachment location is longitudinally spaced along said length of said crotch member from said first terminal edge thereof, and wherein said crotch member comprises a first unattached end portion extending between said first attachment location and said first terminal edge of said crotch member, wherein said first unattached end portion is unattached to said first body panel, and wherein said crotch member is connected to said second body panel at a second attachment location, wherein said second attachment location is longitudinally spaced along said length of said crotch member from said second terminal edge thereof and is located at said first terminal edge of said second body panel, and wherein a second unattached end portion of said crotch member extends between said second attachment location and said second terminal edge of said crotch member, wherein said second unattached end portion is unattached to said second body panel.

14. The undergarment of claim 13 wherein said crotch member comprises a first overlapping portion extending between said first terminal edge of said first body panel and said first terminal edge of said crotch member, wherein said first unattached end portion of said crotch member has a first length and wherein said first overlapping portion of said crotch member have a second length, wherein said first length is at least 20 percent of said second length.

15. The undergarment of claim 13 wherein at least a portion of said second body panel is longitudinally extensible between said first and second longitudinally spaced terminal edges of said second body panel, said second body panel having a longitudinal elongation of at least about 1 cm when subjected to a tensile stress of 11.8 grams/cm and a substantially permanent deformation of at least about 20% when subjected to a tensile stress of 19.70 grams/cm and then allowed to relax under a zero applied stress for a period of about 1 minute, and wherein said second body panel is elastically gathered in a lateral direction between laterally spaced opposite sides of said second body panel.

* * * * *